United States Patent

Landscheidt et al.

Patent Number: 5,231,213
Date of Patent: Jul. 27, 1993

[54] PROCESS FOR THE PREPARATION OF DIALKYL CARBONATES

[75] Inventors: Heinz Landscheidt, Duisburg; Alexander Klausener, Stolberg; Erich Wolters, Köln; Heinz U. Blank, Odenthal-Glöbusch; Udo Birkenstock, Ratingen, all of Fed. Rep. of Germany

[73] Assignee: Bayer Aktiengesellschaft, Leverkusen, Fed. Rep. of Germany

[21] Appl. No.: 910,475

[22] Filed: Jul. 8, 1992

[30] Foreign Application Priority Data

Jul. 17, 1991 [DE] Fed. Rep. of Germany ....... 4123603

[51] Int. Cl.$^5$ .............................................. C07C 68/00
[52] U.S. Cl. ...................................................... 558/277
[58] Field of Search ........................................... 558/277

[56] References Cited

U.S. PATENT DOCUMENTS 4,318,862 3/1982 Romano et al. .................... 558/277
5,162,563 11/1992 Nichihira et al. ................... 558/277

FOREIGN PATENT DOCUMENTS 425197 5/1991 European Pat. Off. .

OTHER PUBLICATIONS

Jiang, Platinum Metal Review, vol. 34 (1990) pp. 178-180.

Primary Examiner—Robert W. Ramsuer
Attorney, Agent, or Firm—Sprung Horn Kramer & Woods

[57] ABSTRACT

Dialkyl carbonates can be prepared by reaction of carbon monoxide with alkyl nitrites in continuous gas phase reaction, in which a platinum metal halide catalyst on aluminum oxides, aluminum oxide hydrates or aluminum hydroxides as support and, if desired, an additive comprising an antimony, bismuth, aluminum, copper, vanadium, niobium, tantalum, tin, iron, cobalt, nickel compound or a mixture of a plurality thereof on this catalyst are used and hydrogen halide is replaced during the course of the reaction batchwise or continuously in at least the amount which is discharged from the reactor together with the reaction mixture. This results in the formation of dialkyl carbonates in almost quantitative selectivity, while the corresponding dialkyl oxalates can not in most cases be detected. The above-mentioned supports are characterized by a BET surface area of more than 1 m$^2$/g.

17 Claims, No Drawings

PROCESS FOR THE PREPARATION OF DIALKYL CARBONATES

BACKGROUND OF THE INVENTION

1. Field of the Invention

The present invention relates to a process for the preparation of dialkyl carbonates by reaction of carbon monoxide (CO) with alkyl nitrites in the presence of a platinum metal halide catalyst on aluminium oxides, aluminium oxide hydrates or aluminium hydroxides as support which may contain additives of compounds of further elements. The aforementioned supports are characterised by a BET surface area of more than 1 $m^2/g$.

Dialkyl carbonates are of general chemical importance. Thus, for example, diethyl carbonate is an excellent solvent in the medium boiling range. Furthermore, dialkyl carbonates are excellent carbonylating and acylating agents. Finally, they are of great importance in the preparation of other carbonates, of urethanes and of ureas.

2. Description of the Related Art

The preparation of dialkyl carbonates by reactions of phosgene or alkyl chloroformates with alcohols is known. However, there is an increasing interest in replacing the use of the toxic phosgene or the intermediates derived therefrom, such as the chloroformic ester, by other processes. In addition to attempts to obtain dialkyl carbonates by reaction of CO with lower alcohols, in particular those processes are important in which CO is reacted in the gas phase with alkyl nitrite over a platinum metal catalyst. In reactions of this type, the formation of dialkyl oxalate is always observed apart from the desired dialkyl carbonate. Thus, EP 425,197 discloses a process which, according to its preferred embodiment, results in dialkyl carbonates of methanol or ethanol from CO and methyl nitrite or ethyl nitrite in the gas phase over a $PdCl_2$ catalyst on activated carbon. The selectivities to give the desired lower dialkyl carbonates reach values of up to 94% according to this EP 425,197, Table 1; however, lower dialkyl oxalates and $CO_2$ are always observed as by-products. Moreover, upon attempting to carry this process in practice, the high selectivities mentioned could only be reproduced insufficiently. The catalysts of this EP 425,197 contain additives of chlorides of base metal; a substantial addition of hydrogen chloride in an amount of 1 to 50%, relative to the platinum metal in the catalyst, is added to the system or a portion of the catalyst must be removed from the reactor and subjected to a treatment with hydrogen chloride.

The Journal for Catalytic Research (China), Vol. 10 (1), p. 75-78 (1989) also uses a carbon support as support for a Pd catalyst so as to obtain dimethyl carbonate from CO and methyl nitrite, in which however dimethyl oxalate is always additionally formed.

A Pd/carbon catalyst is also mentioned in Chin. Sci. Bull. 34 (1989), 875-76 for the preparation of dimethyl carbonate from CO and methyl nitrite.

This preference for a carbon support is not unexpected, since Platinum Metals Review 34 (1990), 178-180 reports with reference to the earlier literature that in the reaction of a lower alkyl nitrite with CO over a Pd catalyst different main products are obtained depending on the support; according to this reference a carbon support predominantly produces dialkyl carbonates, while an $Al_2O_3$ support mainly produces dialkyl oxalates.

SUMMARY OF THE INVENTION

It has now been found that the use of aluminium oxides, aluminium oxide hydrates or aluminium hydroxides as catalyst support does not only lead unexpectedly to dialkyl carbonates when CO is reacted with alkyl nitrites, but moreover additionally also achieved a significant increase in selectivity to give the desired dialkyl carbonates to such an extent that in addition to more than 97% of selectivity, in many cases more than 99% of selectivity to give these dialkyl carbonates, in general it is not possible to detect any oxalate at all. Only a small amount of $CO_2$ can be observed in the reaction mixture. Moreover, the use of $\gamma\text{-}Al_2O_3$ as support, which was not considered possible, has the essential advantage of increased stability and abrasion resistance, compared with a supported catalyst based on a carbon support.

A process for the preparation of dialkyl carbonates of the formula $$O=C(OR)_2 \tag{I}$$

in which
R represents straight-chain or branched $C_1$-$C_4$-alkyl,
by reaction of carbon monoxide (CO) with alkyl nitrites of the formula $$RONO \tag{II}$$

in which
R has the meaning given,
in the presence or absence of an inert gas and in the presence or absence of the parent alcohol ROH and in the presence or absence of NO over a supported platinum metal catalyst at elevated temperature in continuous gas phase reaction has been found, which process is characterised in that the support used comprises aluminium oxides, aluminium oxide hydrates or aluminium hydroxides, the platinum metal is in the form of a halide or a halide-containing complex compound in which the platinum metal halide or the platinum metal halide-containing complex can be formed under the reaction conditions in situ in the process reactor from the platinum metal or a halogen-free platinum metal compound by means of hydrogen halide, the catalyst is furthermore optionally provided with an additive comprising an antimony, bismuth, aluminium, copper, vanadium, niobium, tantalum, tin, iron, cobalt, nickel compound or a mixture of a plurality thereof, and the reaction is carried out at a nitrite:CO volume ratio of 0.1-10:1, preferably 0.2-4:1, especially preferably 0.3-3:1, and a temperature of 50°-150° C., preferably 70°-120° C., especially preferably 70°-110° C., hydrogen halide being replenished batchwise or continuously in at least an amount which is suitable to replace the amount in which hydrogen halide is discharged from the reactor together with the reaction mixture.

DETAILED DESCRIPTION OF THE INVENTION

The reaction in the process according to the invention proceeds according to the following equation:

$$CO + 2RONO \rightarrow O\!:\!C(OR)_2 + 2NO.$$

Examples of straight-chain or branched alkyl having 1-4 C atoms are methyl, ethyl, propyl, isopropyl, butyl, isobutyl, preferably the n-alkyls mentioned, particularly preferably methyl and ethyl and very particularly preferably methyl.

In principle it is possible to start with a mixture of different alkyl nitrites, which however also leads to a mixture of different dialkyl carbonates and, in some cases, unsymmetrically substituted dialkyl carbonates. For a uniform reaction it is therefore preferred to start with only one alkyl nitrite.

While it is in principle possible to react CO with an alkyl nitrite without any further mixture component, for example if the composition of the mixture is outside the explosion limits, an inert gas is in many cases used for diluting the reactants. Examples of inert gases are noble gases, nitrogen and carbon dioxide, preferably argon, nitrogen or carbon dioxide, particularly preferably nitrogen and carbon dioxide. The amount of inert gas is 20-80% by volume, preferably 30-70% by volume, relative to the entire gas volume to be introduced into the reactor. The inert gas and any unconverted residual amounts of the reactants contained therein can be recycled.

The volume ratio of the reactants nitrite and CO to one another is 0.1-10:1, preferably 0.2-4:1, particularly preferably 0.3-3:1.

The gas mixture to be reacted can furthermore contain small amounts of alcohol ROH, for example in an amount of 0-10% by volume, and small amounts of NO, for example in an amount of 0-10% by volume, both relative to the entire volume of the gas mixture to be used. These additions of ROH or NO can originate, for example, from the preparation of the alkyl nitrite and be introduced, for example, together with the latter into the reaction gas mixture. The catalyst support according to the inventive process comprises aluminium oxide, aluminium oxide hydrate or aluminium hydroxide or a mixture of more than one of these compounds or it has a content thereof. The content of said compounds is 1-100% by weight of the support as a whole. Values below 100% by weight are a result of standard contents of natural impurities or impurities resulting from the method of manufacture of the above compounds. Such impurities, e.g. $SiO_2$, $Fe_2O_3$, $TiO_2$, CaO, MgO, $Na_2O$, $K_2O$, $B_2O_3$ or a combination of more than one of these compounds, or inorganic sulphates, carbonates and/or chlorides, are in some cases only present in trace amounts. The contents of the abovementioned aluminium oxides, aluminium oxide hydrates or aluminium hydroxides in the supports are preferably 80-100% by weight and particularly preferably 90-100% by weight. Other values below 100% by weight apply in the case of support preparations in which the abovementioned aluminium compounds are applied to other supports such as $SiO_2$, $TiO_2$, pumice, $CaCO_3$, $BaSO_4$, etc. and envelope such supports in the form of shells. In this case the contents of the abovementioned aluminium compounds are 1-60% by weight, and preferably 1-30% by weight, of the support preparation.

The BET surface area of the abovementioned aluminium compounds is higher than 1 $m^2/g$, and is preferably 10 $m^2/g$ or more, particularly preferably 50 $m^2/g$ or more, and most preferably 100 $m^2/g$ or more. The upper value for the BET surface area can be as high as up to 500 $m^2/g$ or more, and most preferably up to 400 $m^2/g$ or more. The aluminium oxides, aluminium oxide hydrates and aluminium hydroxides are defined by the general formula $$Al_2O_{3-n}(OH)_{2n} \cdot mH_2O$$

in which
n denotes one of the integers 0, 1, 2 or 3 and
m has a value from 0 to 10, preferably from 0 to 5.

The expression $mH_2O$ refers to the removable water phase, which in many cases does not take part in the formation of the crystal lattice, so that m can also have values which are not integers. On calcinating such support materials m can reach the value zero.

One important aluminium compound is $\gamma$-$Al_2O_3$.

Many of the abovementioned support materials are commercially available, such as for example SPH-501, -508, -517, -535 and -537 from Rhone-Poulenc; CS-331/1, -331/3 and -331/5 from Südchemie; GS-2261/1, -2261/2 and -2261/3 from Kalichemie; Pural-S/SB 30, -S/SB 50, -S/SB 70 and TKA-168 from Condea; D 10-10 from BASF; A 980 from Hoechst CeramTec and L 22 from Girdler.

The reactive component of the catalyst for the process according to the invention comprises in its reactive state the platinum metal halide or a complex compound containing the platinum metal halide. Complex compounds of this type are generally known and are, for example, alkali metal chloride complex compounds, such as lithium tetrachloropalladate or sodium tetrachloropalladate, $Li_2[PdCl_4]$ or $Na_2[PdCl_4]$.

Furthermore, it has been found that the platinum metal halide or the complex compound containing the platinum metal halide can also be formed under the reaction conditions, i.e. in the presence of the gas mixture to be reacted, in situ from metallic platinum metal or a halogen-free platinum metal compound by means of hydrogen halide. Accordingly, the reactor can also be filled with an otherwise comparable catalyst containing the platinum metal initially in metallic form or prepared by means of a halogen-free platinum metal compound. Examples of suitable halogenfree platinum metal compounds of this type are platinum metal acetates, nitrates, propionates, butyrates, carbonates, oxides, hydroxides or others known to one skilled in the art.

Elements from the group of platinum metals according to the invention are Pd, Pt, Ir, Ru and Rh, preferably Pd, Ru and Rh, and particularly preferably Pd.

Halides according to the invention are fluoride, chloride, bromide and iodide, preferably chloride and bromide and particularly preferably chloride.

The amount of the platinum metal halide or the complex compound containing the platinum metal halide is 0.01-8% by weight, preferably 0.05-4% by weight, calculated as platinum metal and based on the overall weight of the catalyst.

The catalyst for the process according to the invention is furthermore optionally provided with an additive comprising an antimony, bismuth, aluminium, copper, vanadium, niobium, tantalum, tin, iron, cobalt, nickel compound or a mixture of a plurality thereof; preferably, such an additive is present. Such additives are present in salt-like or metallic form of the elements mentioned. In a manner similar to that described above for the platinum metal, the halide form, for example, of such additives if formed from the metallic form of these additives and hydrogen halid under the reaction conditions. Preferably, such additives comprise an antimony, bismuth, aluminium, vanadium, niobium, tantalum compound or a mixture of a plurality thereof, particularly preferably they comprise a halide of these elements, very particularly preferably a chloride of these elements. The amount of additive is 0.1-100 times, preferably 0.2-10 times, the amount of the platinum metal calculated as metal not only for the additive but also for the platinum metal.

A catalyst to be used according to the invention is prepared by methods which are generally known to one skilled in the art. Thus, the support can be impregnated or sprayed with a solution of one of the platinum metal compounds mentioned. The same procedure is used for the additive(s) mentioned. In the case where it is desired to fix the platinum metal as a metal or in the form of the carbonate, oxide or hydroxide on the support and only to activate it in the reactor under the reaction conditions in the manner described by means of hydrogen halide to give platinum metal halide, the platinum metal compound applied can be reduced to the metal by means of a suitable reducing agent in a manner known to one skilled in the art or converted into the carbonate, oxide or hydroxide by means of a suitable precipitant.

Examples of the many methods of preparing the catalysts or catalyst supports which can be used according to the invention are as follows:

1. producing mouldings from the abovementioned oxidic and hydroxyoxidic aluminium compounds,
2. incorporating the catalytically active components, such as the abovementioned platinum metals or compounds thereof, as well as, where appropriate, the abovementioned additives into the basic composition of the support prior to moulding,
3. subsequently loading the finished mouldings by impregnation, immersion or spraying, using salts of the platinum metals and, where appropriate, of the additional elements,
4. rolling or spraying oxidic or hydroxyoxidic aluminium compounds onto agglomerates of any desired composition and origin,
5. rolling or spraying oxidic or hydroxyoxidic aluminium compounds already containing incorporated platinum metals or compounds thereof, as well as, where appropriate the abovementioned additives according to 2, onto the agglomerates according to 4, or
6. subsequently loading the supports produced according to 4 as described under 3.

Furthermore, it has been observed that in order to achieve uniformly high selectivities of dialkyl carbonate, it is advantageous to transport hydrogen halide to the catalyst while it is in use. However, it has further been observed that this amount of hydrogen halide can be significantly less than described in the literature, as mentioned above. Thus, it is only necessary to replenish the amount of hydrogen halide originating from the active form of the catalyst and discharged together with the reaction products. This amount can be determined by analysis. It is in general in the range from 50-5,000 ppm of hydrogen halide in the reactant gas mixture.

Hydrogen halide according to the invention is hydrogen fluoride, hydrogen chloride, hydrogen bromide and hydrogen iodide, preferably hydrogen chloride and hydrogen bromide, and particularly preferably hydrogen chloride.

Hydrogen halide can be metered into the reaction mixture as such in gaseous form. However, it can also be metered in dissolved in one of the substances present in the reaction mixture, thus, for example, dissolved in the alcohol on which the alkyl nitrite is based.

Catalysts of the type described have a long life (>200 h). In addition to the mechanical stability and abrasion resistance already described, they retain their activity and selectivity over an exceptionally long period.

The gas hourly space velocity (GHSV) over the catalyst mentioned can be 700-17,000 l of mixture of the gaseous reactants per l of catalyst per hour.

The process according to the invention is carried out at a temperature of 50°-150° C., preferably 70°-120° C., particularly preferably 70°-110° C., and a pressure of 0.8-10 bar, preferably 1-7 bar, particularly preferably 1-6 bar.

The alkyl nitrites to be used according to the invention are prepared by known processes, for example from the corresponding alcohol and nitrous acid, which is formed for example in situ, from an alkali metal nitrite and a mineral acid, such as sulphuric acid. The nitrogen monoxide NO formed during the course of the process according to the invention can be regenerated continuously using oxygen and new alcohol to give alkyl nitrite (German Offenlegungsschrift 3,834,065) and recycled together with unconverted reactants.

EXAMPLES

DEFINITIONS

The space-time yield (STY) in [g/lxh] and the yield of dimethyl carbonate in the examples is calculated by $$\frac{m_{DMC}}{v_{Cat} \times t},$$

in which $m_{CMC}$ is the amount of dimethyl carbonate (DMC) formed, $v_{Cat}$ is the catalyst volume and t the time.

The selectivity S (%) for dimethyl carbonate is calculated by $$S = \frac{n_{DMC}}{n_{DMC} + 2 \times n_{ODME} + n_{AME} + n_{FDA}} \times 100$$

in which
$n_{DMC}$ is the amount of dimethyl carbonate,
$m_{ODME}$ is the amount of dimethyl oxalate,
$n_{AME}$ is the amount of methyl formate,
$n_{FDA}$ is the amount of formaldehyde dimethyl acetal.

COMPARATIVE EXAMPLE 1 (VIDE EP 425,197)

100 ml of activated carbon granules were impregnated in a known manner with a solution of $PdCl_2$ and $CuCl_2$ in water, and the product was dried at 80° C. in vacuo (20 mm Hg). The ready-to-use catalyst contained 8 g of Pd/l and 8 g of Cu/l.

EXAMPLE 1

100 ml of an $Al_2O_3$ with a BET internal surface of 185 m²/g were impregnated with an aqueous $Li_2PdCl_4$ solution, and the product was dried at 80° C. in vacuo (29 mm hg). The catalyst then contained 8 g of Pd/1.

Description of the process

In an upright glass tube, the respective catalyst was placed between a packing of Raschig rings.

The glass tube was heated to 90° C., and was fed with a gas mixture comprising HCl, $CO_2$, $CH_3ONO$, CO and $CH_3OH$. The gas leaving the reactor was cooled to 5°

C., and the condensed phase obtained was analysed by gas chromatography. The uncondensed products were detected by means of IR spectroscopy and mass spectroscopy.

TABLE

Examples 2 and 3; Comparative Examples 2 and 3 (according to the description of the process)

| Example | Catalyst | Reactant Gas Mixture (% by vol.) | | | | | GHSV* ($h^{-1}$) | STY** | S** | STY*** | S*** |
|---|---|---|---|---|---|---|---|---|---|---|---|
| | | CO | $CH_3ONO$ | $CH_3OH$ | $CO_2$ | HCl (ppm) | | | | | |
| Comp. Ex. 2 | from Comp. Ex. 1 | 22.5 | 22.5 | 5 | 50 | 1,100 | 800 | 120 | 97.0 | 100 | 95.0 |
| Example 2 | from Example 1 | 22.5 | 22.5 | 5 | 50 | 1,100 | 800 | 330 | 99.8 | 330 | 99.8 |
| Comp. Ex. 3 | from Comp. Ex. 1 | 25 | 26 | 6.5 | 42.5 | 1,100 | 2,400 | 480 | 97.0 | 370 | 94.0 |
| Example 3 | from Example 1 | 25 | 26 | 6.5 | 42.5 | 1,100 | 2,400 | 1,030 | 99.8 | 1,020 | 99.8 |

*GHSV = Gaseous Hourly Space Velocity
**after ½ hour
***after 10 hours

What is claimed is:

1. A process for the preparation of a dialkyl carbonate of the formula $$O=C(OR)_2$$

in which

R represents straight-chain or branched $C_1$–$C_4$-alkyl, by reaction of carbon monoxide (CO) with an alkyl nitrite of the formula

RONO in which

R has the meaning given,
in the presence or absence of an inert gas and in the presence or absence of the parent alcohol ROH and in the presence or absence of NO over a supported palladium metal catalyst at elevated temperature in continuous gas phase reaction, wherein the support used is an aluminum oxide, an aluminum oxide hydrate or an aluminum hydroxide having a BET internal surface of more than 1 $m^2$/g, the palladium metal is in the form of a halide or a halide containing complex compound, in which the palladium metal halide or the palladium metal containing halide complex compound can be formed under the reaction conditions in situ in the process reactor from the palladium metal or a halogen-free palladium metal compound by means of hydrogen halide, the catalyst furthermore can be provided with an additive comprising an antimony, bismuth, aluminum, copper, vanadium, niobium, tantalum, tin, iron, cobalt, nickel compound or a mixture of a plurality thereof, and the reaction is carried out at a nitrite:CO volume ratio of 0.1–10:1 and a temperature of 50°–150° C., hydrogen halide being replenished batchwise or continuously at least in the amount which is suitable to replace the amount in which it is discharged from the reactor together with the reaction mixture.

2. The process of claim 1, wherein the reaction is carried out at 70°–120° C.

3. The process of claim 2, wherein the reaction is carried out at 70°–110° C.

4. The process of claim 1, wherein the reaction is carried out at a nitrite:CO volume ratio of 0.2–4:1.

5. The process of claim 4, wherein the nitrite:CO columne ratio is 0.3–3:1.

6. The process of claim 1, wherein the catalyst support consists of 1–100% by weight of the total support of the oxidic or hydroxyoxidic Al compound.

7. The process of claim 1, wherein the BET internal surface is 10 $m^2$/g or more, 8. The process of claim 7, wherein the BET internal surface is 50 $m^2$/g or more.

9. The process of claim 8, wherein the BET internal surface is 100 $m^2$/g or more.

10. The process of claim 1, wherein the halogen in the halide and in the hydrogen halide is fluorine, chlorine, bromine or iodine.

11. The process of claim 10, wherein the halogen is chlorine or bromine.

12. The process of claim 11, wherein the halogen is chlorine.

13. The process of claim 1, wherein the replenished hydrogen halide is of an amount of 50–5,000 ppm, based on the reactand gas mixture.

14. The process of claim 1, wherein the reaction is carried out in the presence of an inert gas, the amount of inert gas being 20–80% by volume of the overall gas volume.

15. The process of claim 1, wherein dimethyl carbonate or diethyl carbonate is prepared by reaction of CO with methyl nitrite or ethyl nitrite.

16. The process of claim 15, wherein dimethyl carbonate is prepared by reaction of CO with methyl nitrite.

17. The process of claim 1, wherein the reaction is carried out at a pressure of 0.8–10 bar.

* * * * *